(12) United States Patent
Bagdi et al.

(10) Patent No.: US 7,001,603 B2
(45) Date of Patent: Feb. 21, 2006

(54) GELLED TWO PHASE COSMETIC COMPOSITIONS

(75) Inventors: Zsolt Bagdi, Glen Cove, NY (US); Peter J. Lentini, Bayside, NY (US)

(73) Assignee: Color Access, Inc., Melville, NY (US)

(*) Notice: Subject to any disclaimer, the term of this patent is extended or adjusted under 35 U.S.C. 154(b) by 0 days.

(21) Appl. No.: 09/796,203

(22) Filed: Feb. 28, 2001

(65) Prior Publication Data
US 2002/0160023 A1    Oct. 31, 2002

(51) Int. Cl.
A61K 6/00         (2006.01)
A61K 31/045     (2006.01)

(52) U.S. Cl. ............... 424/401; 514/506; 514/724; 514/944

(58) Field of Classification Search ........... 424/401, 424/489, 420, 455; 514/506, 724
See application file for complete search history.

(56) References Cited

U.S. PATENT DOCUMENTS

| | | | |
|---|---|---|---|
| 5,314,685 A * | 5/1994 | Tyle et al. ............... 424/401 |
| 5,422,363 A * | 6/1995 | Yanai et al. ............. 514/410 |
| 5,641,809 A * | 6/1997 | Hagen et al. ............ 514/558 |
| 5,679,326 A * | 10/1997 | Bara et al. .............. 424/70.1 |
| 5,718,890 A * | 2/1998 | Putnam et al. ........... 424/65 |
| 5,750,124 A * | 5/1998 | Gohla et al. ............ 424/401 |
| 6,022,559 A * | 2/2000 | Simonnet ................ 424/450 |

OTHER PUBLICATIONS

Yoshino, N. et al., (2000) JP 2000219617 A2, Abstract.*
Sato, F. et al., (2000) JP 2000212049 A2, Abstract.*
Sato, F. et al., (1998) JP 10273433 A2, Abstract.*
Knowlton, J.L., "Emulsion Theory", Poucher's Perfumery, Cosmetic, and Soaps (2000, 10$^{th}$ ed. by Hllda Butler), Kluwer Academic Publishers, pp. 609-610.*
Porter et al., Handbook of Surfactants, (1991, 1st ed.) Blackie and Son Ltd. p. 117.*

* cited by examiner

Primary Examiner—Sreeni Padmanabhan
Assistant Examiner—Gina C. Yu
(74) Attorney, Agent, or Firm—Mekalaradha Masilamani

(57) ABSTRACT

The present invention relates to anhydrous two phase emulsified composition comprising a nonaqueous hydrophilic external phase, and an internal oil phase, each phase being gelled by a condensation product of glycerine and a long chain fatty acid.

11 Claims, No Drawings

GELLED TWO PHASE COSMETIC COMPOSITIONS

FIELD OF THE INVENTION

The present invention relates to cosmetic compositions. More particularly, the invention relates to cosmetic emulsions.

BACKGROUND OF THE INVENTION

Exfoliating scrubs are used by a wide variety of consumers. These products typically contain mild abrasives, such as wax particles or nut shell powders, that gently remove dead skin cells, leaving the skin underneath smooth and fresh. Many of these products, however, are primarily soap-based, and therefore can be drying to certain skin types. A currently popular alternative is an exfoliating rub containing such physical exfoliants suspended in an oily base. Products of this type are typically used in or after a shower, not only to scrub away dead skin, but also to simultaneously provide an emollient effect to the skin by virtue of the high oil content. While such products are very effective, leaving the user's skin feeling exceptionally smooth and moisturized, they have certain disadvantages. The oily base is generally relatively thin, and therefore can run through the fingers when application is attempted, resulting in some waste of the product. The suspended solids can also settle out, requiring the user to remix the product each time it is used. In addition, the presence of the oil base can present challenges in packaging, since there can be a tendency for the oil to leak through traditional closures.

In a search for a solution to the aforementioned difficulties, it has been unexpectedly found that a novel emulsion system can provide a base for similar products having substantially the same effect as the original rubs, while avoiding the disadvantages. The novel emulsion also is surprisingly effective as a moisturizing cleanser, even without the presence of the exfoliating solids, and therefore provides a particularly useful base for a wide range of cosmetic products.

SUMMARY OF THE INVENTION

The present invention provides an anhydrous two phase emulsified composition comprising a nonaqueous hydrophilic external phase, and an internal oil phase, each phase being gelled by a condensation product of glycerine and a long chain fatty acid. In one embodiment the composition comprises one or more suspended solids in the external phase, e.g., a physical exfoliating agent.

DETAILED DESCRIPTION OF THE INVENTION

The compositions of the invention provide a unique type of emulsified product which provides long-term stability, even in the presence of substantial quantities of additive materials, particularly large quantities of solids. The primary components of the composition comprise a substantially nonaqueous but hydrophilic external phase, and a dispersed internal oil phase. Each phase of the composition is gelled by a condensation product of glycerine and a long-chain fatty acid. The resulting products are not only stable but also provide an unusual level of moisturization to the skin to which it is applied.

The hydrophilic phase comprises a glycol as its main component. Examples of useful glycols for the present purpose are butylene glycol, propylene glycol, isoprene glycol, pentylene glycol, hexylene glycol, glycerine, diglycerine or polyglycerine, or combinations thereof. Particularly preferred as the hydrophilic base is glycerine. The hydrophilic phase, including the base and its hydrophilic additives, ordinarily will comprise from about 25% to about 95% of the composition as a whole, with at least about 30% of that amount being a glycol.

The oil portion of the emulsion preferably includes one or more cosmetically acceptable oils or oil-like emollients. Any cosmetically or pharmaceutically acceptable oil may be used as the oil. Examples of suitable oils or oil-like emollients can be found in the International Cosmetic Ingredient Handbook, CTFA, 2000, the contents of which are incorporated herein by reference. Useful materials include, but are not limited to, hydrocarbon oils, such as isoparaffins, squalane, or petrolatum; animal oils, such as mink oil, lanolin and lanolin derivatives, or cholesterol; C10–18 triglycerides; esters having the formula RCO-OR' wherein RCO represents a carboxylic acid radical and OR' represents an alcohol residue, such as isodecyl neopentanoate, tridecyl octanoate, cetyl palmitate, cetyl octanoate, cetyl stearate, cetyl myristate, isopropyl palmitate, isopropyl myristate, polyglyceryl-2-isostearate, neopentyl glycol distearate, isodecyl oleate, decyl isostearate, diisopropyl sebacate, PEG-4 diheptanoate, dioctyl malate, and isohexyl neopentanoate; fatty alcohols, such as lanolin alcohol or oleyl alcohol; and silicone oils, such as cyclomethicone, dimethicone, phenyl trimethicone, cetyl dimethicone, lauryl trimethicone, and dimethiconol.

Particularly preferred oils, either alone or in combination, however, are vegetable or plant derived oils, such as castor oil, coconut oil, jojoba oil, corn oil, avocado oil, sunflower oil, cottonseed oil, palm kernel oil, soybean oil, olive oil, walnut oil, meadownfoam seed oil, wheat germ oil, grape seed oil, sesame seed oil, almond oil, peach kernel oil, orange oil, lemon oil, shea butter, or illipe butter. A particularly preferred vegetable oil is olive oil. In the present compositions, the oil phase will constitute about 10% to about 75%, preferably about 20 to about 40% by weight of the composition, of one or more oils Each phase of the emulsion is gelled by a gellant that is a condensation product of a glycerine component and a long chain fatty acid. The glycerine component may be glycerine, diglycerine, or a polyglycerine of up to 10 glycerine moieties. The fatty acid component may be selected from C12–C 22 fatty acids, or combinations thereof. Examples of fatty acid components include, but are not limited to, linoleate, behenate, eicosanoate, laurate, myristate, palmitate. Particularly preferred is a combination of behenate and eicosanoate.

Although both phases are gelled by condensation products of this type, the specific identity of the gellants used for the respective phases will differ. Depending on the number of glycerine moieties present, the gellant may be more polar or more hydrophobic, and more compatible with the hydrophilic or oil phase, respectively. Therefore, the choice of gellant is made by selecting the gellant in accordance with its hydrophilicity or hydrophobicity. Generally speaking, the gellants with lower numbers of glycerin moieties, i.e., up to about 3, are more appropriate for gelling the oil phase, whereas the presence of greater numbers of glycerine units, i.e., at least 4 or more, renders the gellant more appropriate for gelling the hydrophilic phase. Particularly preferred gellants are glyceryl behenate/eicosadioate for the oil phase, and polyglyceryl-10 behenate/eicosadioate for the hydrophilic phase. These products are commercially available from Ikeda Corp., under the trade names Numcort HK-G and Numcort HK-P, respectively. The amounts of gellant used will depend upon the desired consistency of the final product, and therefore, the amounts are not critical; however, in most cases, the gellants are each used in their respective phases in an amount of about 0.25 to about 25% by weight of the composition, and preferably from about 1 to about 10% by weight Although not essential, it is often preferred, particularly when using a vegetable oil as the primary component of the oil base, to use a neutralizing compound to neutralize the free fatty acids that constitute a portion of vegetable oils. The reaction between the neutralizing compound and fatty acid forms a soap which not only aids in gelling, but also provides a cleansing function. Useful neutralizing agents include, but are not limited to, sodium hydroxide, triethanolamine, and aminomethyl propanediol(AMPD). Particularly preferred for use in the present compositions is AMPD, in an amount of from about 0.1 to about 5% by weight of the composition.

It may also be desirable to provide additional moisturizers and emollients to the compositions, to further enhance its moisturizing capacity. Examples of useful materials for this purpose include, but are not limited to, esters, waxes, glycerides, petrolatum, oils, and the like. A more detailed listing of such materials can be found in the International Cosmetic Ingredient Dictionary and Handbook, Eighth Edition, 2000, the contents of which are incorporated herein by reference.

The compositions of the invention provide a particularly useful base for cleansing and conditioning the skin. The compositions are applied dry to the skin, and then water added directly to the treated areas. Upon contact and light rubbing of the wetted composition, the product "blooms", providing a conditioning cream or lotion that can be further rubbed into the skin, and then rinsed off with additional water. After rinse-off, the skin is left remarkably moisturized and soothed The compositions do not strip the protective lipid layer, as other cleansers can do, nor do they contain high levels of potentially irritating emulsifiers. Therefore, the compositions can be readily used, even on a daily basis, by individuals with very dry or sensitive skin, as well as by those with normal skin.

The formulations prepared as described above are effective cleansers and/or skin conditioners, and can also be used as the base for make-up removers or shaving gels. However, it may be desirable to provide additional components to the formulations to enhance their functionality. To this end, in one embodiment, the formulations incorporate solids into the external phase in order to provide a scrubbing or exfoliating effect. The solids employed can be any pharmaceutically or cosmetically acceptable particulate materials that can be rubbed against the skin to remove dirt and dead cells from the skin surface. Examples of materials that are typically used for this purpose include, but are not limited to, salts, sugar, waxes with a melting point of greater than about 70° C., including natural waxes such as carnauba, ozokerite, montan wax, or beeswax or synthetic waxes, such as polyethylene and synthetic carnauba; fruit and vegetable derivatives, such as almond meal, apricot shell powder, corn flour, corn meal, pecan shell powder, peach pit powder, walnut shell powder, and luffa, and mineral abrasives, such as diatomaceous earth, hydrated silica, and hydroxyapatite. Surprisingly, the emulsions of the invention are stable enough to accommodate relatively large proportions of solids. The amount of solids used can range from about 1 to about 70%. The formulations can also incorporate a significant amount of fragrance, which may be added in an amount of up to about 20% by weight.

A variety of other additives can also be provided in the composition. It may be desirable to incorporate "blooming agents" which, when the product is on the skin, assist in bringing water into the product and spreading on the skin, and contributing to the whitening bloom that characterizes the product. A typical blooming agent will be a surfactant with an HLB at the lower end of the HLB scale.

The formulations can also incorporate active ingredients into the two phases. Examples of possible actives include, but are not limited to, antioxidants, anti-aging and anti-wrinkle compounds, antimicrobials, sunscreens, self-tanners, chemical exfoliants, whitening agents, vitamins, anti-acne agents, anti-irritants, anti-inflammatories, hormones, moisturizers, hair conditioning and treatment agents, and the like. Those skilled in the art will readily recognize other components that can beneficially be applied in the bases of the present invention.

The invention is further illustrated by the following non-limiting examples.

EXAMPLES

Example 1

A formulation according to the present invention is prepared as follows:

| Material | Wt. % |
| --- | --- |
| Phase I | |
| Glycerine | 53.00 |
| Polyglyceryl-10 behenate/eicosadioate | 5.00 |
| PEG-10 sunflower glycerides | 2.00 |
| Polyglyceryl-3 beeswax | 2.00 |
| Glyceryl monostearate | 1.00 |
| Aminomethyl propanediol | 0.50 |
| Phase 2 | |
| Olive oil | 23.50 |
| Glyceryl behenate/eicosadioate | 3.00 |
| Phase 3 | |
| Orange oil | 10.00 |

In the main vessel, the Phase 1 ingredients are added one at a time in sequence and combined with a propeller mixer at about 200 rpm, with heating to 80° C. at the addition of the glycerides. The components are mixed until all solids are completely dissolved and the mixture is uniform. The main vessel is allowed to cool to 75° C. In a supplemental vessel, the Phase 2 ingredients are combined by propeller mixing at about 150 rpm and heated to a temperature of 70° C. Phase 2 is mixed to homogeneity, and the temperature is adjusted to 60° C. Phase 3 is then added to Phase 2 and the combined materials mixed until uniform. Combined phases 2 and 3 are added to the main and processed by homogenizer at about 2000–2800 rpm for about 30 minutes.

Example 2

A second formulation, containing exfoliating solids, is prepared as follows:

| Materials | Wt. % |
|---|---|
| Glycerine | 25.00 |
| Polyglyceryl-10 behenate/eicosadioate | 2.50 |
| PEG-10 sunflower glycerides | 1.00 |
| Polyglyceryl-3 beeswax | 1.50 |
| Glyceryl monostearate | 0.25 |
| Aminomethyl propanediol | 0.25 |
| Phase 2 | |
| Olive oil | 12.50 |
| Sunflower oil | 2.50 |
| Meadowfoam seed oil | 2.00 |
| Glyceryl behenate/eicosadioate | 1.00 |
| Grape seed oil | 0.50 |
| Phase 3 | |
| Fragrance | 1.00 |
| Phase 4 | |
| Sucrose | 35.00 |
| Sodium chloride | 15.00 |

This composition is prepared substantially as described above, with alternate additions of the solids as the last step.

What we claim is:

1. A cosmetically or pharmaceutically acceptable anhydrous two phase emulsified composition comprising a non-aqueous hydrophilic external phase containing polyglyceryl-10 behenate/eicosanedioate as a gellant and an internal oil phase containing glyceryl behenate/eicosadioate as a gellant.

2. The composition of claim 1 in which the external phase comprises a glycol selected from the group consisting of butylene glycol, propylene glycol, isoprene glycol, pentylene glycol, hexylene glycol, glycerine, diglycerine, polyglycerine, and mixtures thereof.

3. The composition of claim 2 in which the external phase comprises glycerine.

4. The composition of claim 1 in which the oil phase comprises an oil selected from the group consisting of hydrocarbons, animal oils, vegetable oils, esters, fatty alcohols and silicone oils, and mixtures thereof.

5. The composition of claim 4 in which the oil phase comprises at least one vegetable oil.

6. The composition of claim 1 which also comprises a neutralizing agent.

7. The composition of claim 6 in which the neutralizing agent is aminomethyl propanediol.

8. The composition of claim 1 which also comprises at least one exfoliating solid.

9. A cosmetically or pharmaceutically acceptable anhydrous two phase emulsified composition comprising a non-aqueous hydrophilic external phase containing a hydrophilic phase gellant, the gellant being polyglyceryl-10 behenate/eicosanedioate, the hydrophilic phase containing glycerine, and an internal oil phase containing an oil phase gellant, the gellant being glyceryl behenate/eicosanedioate, the oil phase comprising a vegetable oil.

10. The composition of claim 9 which comprises a neutralizing agent.

11. The composition of claim 9 which comprises at least one exfoliating solid.

* * * * *